United States Patent [19]

Haas et al.

[11] 4,182,805

[45] Jan. 8, 1980

[54] DECYANATION

[75] Inventors: Howard C. Haas, Arlington, Mass.;
Robert D. Moreau, Nashua, N.H.

[73] Assignee: Polaroid Corporation, Cambridge, Mass.

[21] Appl. No.: 911,445

[22] Filed: Jun. 1, 1978

Related U.S. Application Data

[63] Continuation-in-part of Ser. No. 725,571, Sep. 22, 1976, Pat. No. 4,110,424, which is a continuation-in-part of Ser. No. 627,373, Oct. 30, 1975, abandoned.

[51] Int. Cl.$^2$ .............................................. C08F 8/30
[52] U.S. Cl. ..................................... 525/336; 525/359
[58] Field of Search ..................................... 526/23, 46

[56] References Cited

U.S. PATENT DOCUMENTS

| | | | |
|---|---|---|---|
| 3,983,097 | 9/1976 | Okubo et al. | 526/23 |
| 4,046,766 | 9/1977 | Costin | 526/23 |

FOREIGN PATENT DOCUMENTS

| | | | |
|---|---|---|---|
| 228090 | 6/1968 | Australia | 526/23 |
| 654267 | 6/1951 | United Kingdom | 526/23 |

*Primary Examiner*—William F. Hamrock
*Attorney, Agent, or Firm*—Esther A. H. Hopkins

[57] ABSTRACT

Processes are disclosed for providing in situ generated cyanic acid and simultaneously preparing certain carboxamides which have a tertiary aliphatic substituted ammonium or pyridinium group substituted on the alpha carbon atom.

3 Claims, 1 Drawing Figure

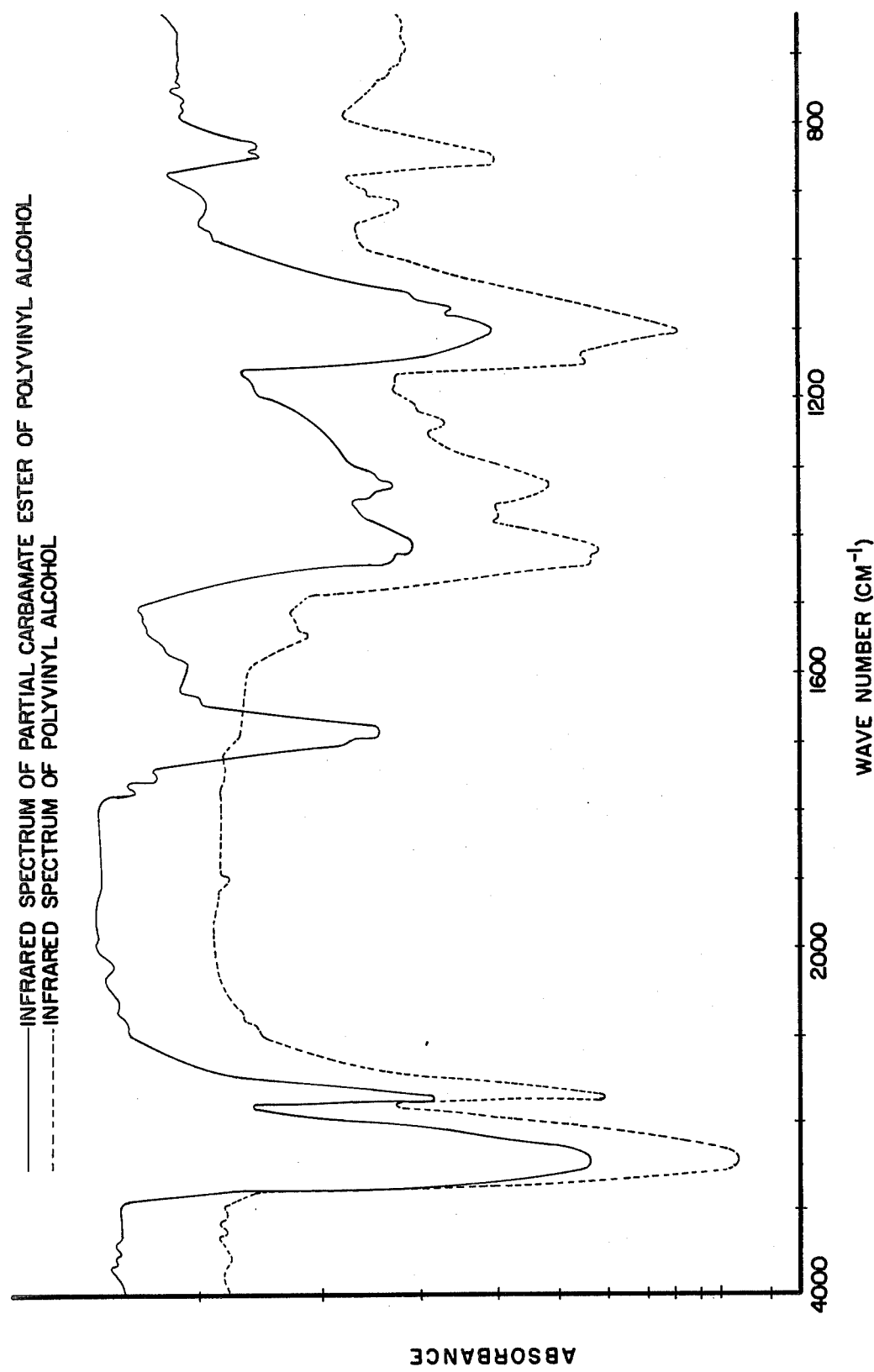

DECYANATION

This is a continuation-in-part of Ser. No. 725,571 filed Sept. 22, 1976, now U.S. Pat. No. 4,110,424, which is a continuation-in-part of Ser. No. 627,373, filed Oct. 30, 1975 now abandoned, in the names of Howard C. Haas and Robert D. Moreau.

This invention relates to novel polymeric quaternary salts which can be used to produce cyanic acid and polymeric carboxamides. The current available way to provide cyanic acid is by cracking cyanuric acid and stabilizing the resulting cyanic acid. Cyanic acid is volatile and polymerizes explosively unless properly stabilized. Providing it for in situ reaction removes the problem of handling it.

Most organic acids undergo decarboxylation if they are heated to a sufficiently high temperature. The presence of strongly electron withdrawing substituents on the α-carbon atom greatly facilitates the ease with which carbon dioxide is released. The decarboxylation reaction is normally heterolytic, the R group departing with an electron pair.

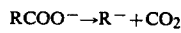

Enol forms of the acid are not generally involved in decarboxylation. With β-carbonyl containing acids, cyclic hydrogen bonded structures, however, are believed to play a role in the decarboxylation mechanism. The decarboxylation of malonic acid, for example, is usually written as:

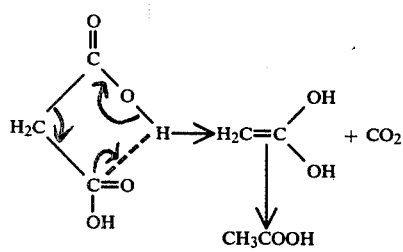

The pyrolysis of amides is generally a very complex reaction. Upon heating they can dehydrate to form nitriles and, in some cases, ammonia is split out to yield imides, particularly if stable cyclic imides are possible.

It is the primary object of the present invention to provide a novel method of decyanating quaternary salts of certain amides containing highly positively polarized α-carbon atoms to form α-pyridinium carboxamides. It is, further, an object of this invention to provide a source for generating, in situ, cyanic acid.

Other objects of the invention will in part be obvious and will in part appear hereinafter.

The invention accordingly comprises the method involving the several steps and the relation and order of one or more of such steps with respect to each of the others which are exemplified in the following detailed disclosure, and the scope of the application of which will be indicated in the claims.

For a fuller understanding of the nature and objects of the invention, reference should be had to the following detailed description taken in connection with the accompanying drawing wherein:

FIG. 1 is a graphic representation of the infrared spectrum of polyvinyl alcohol (the dashed curve) and of the partial carbamate ester of polyvinyl alcohol (the solid curve).

It has now been discovered that certain organic amides which contain highly positively polarized α-carbon atoms preferentially lose cyanic acid on heating. This reaction involves the thermal loss of cyanic acid (HOCN⇌HNCO) by an amide in much the same manner that an organic acid loses carbon dioxide during decarboxylation. The reaction will be referred to as a decyanation. This decyanation proceeds in a manner which is completely analogous to the decarboxylation of malonic acid. The reaction provides a useful way of providing cyanic acid in situ for use in reactions utilizing cyanic acid.

Compounds of the following structure may be decyanated according to this invention

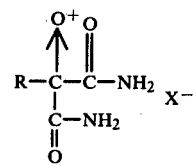

where R is selected from one group consisting of hydrogen and alkyl groups containing from one to twenty carbon atoms inclusive, Q is selected from the group consisting of tertiary aliphatic substituted ammonium groups, polymeric tertiary aliphatic substituted ammonium groups, pyridinium, substituted pyridinium, polymeric substituted pyridinium, quinolinium and iso quinolinium where R is hydrogen and from the group consisting of pyridinium, substituted pyridinium, polymeric substituted pyridinium and iso quinolinium groups when R is alkyl, and X is selected from the group consisting of bromide, chloride and iodide.

The following polymeric compounds are included in this formula

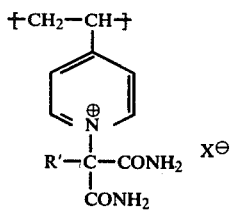

and

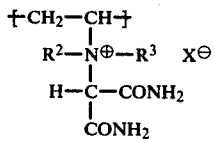

wherein R' is selected from the group consisting of hydrogen and n-alkyl groups containing from one to twenty carbon atoms inclusive, $R^2$ and $R^3$ are lower alkyl groups having from one to four carbon atoms and X is as defined above.

As noted, n-alkyl groups may contain from one to twenty carbon atoms inclusive, as for example, methyl, ethyl, n-propyl, n-butyl, n-decyl, n-dodecyl and the like. When R is n-decyl, and Q is pyridinium, for example, the α-pyridinium carboxamide formed by way of this invention is useful as a wetting agent.

Examples of these compounds are the pyridine or isoquinoline quaternary salts of 2-bromomalonamide, 2-methyl-2-bromomalonamide or 2-n-decyl-2-bromomalonamide; the polymeric quaternary salts prepared by quaternizing poly 4-vinyl pyridine with bromomalonamide; the trimethyl ammonium salt of bromomalonamide; the p-phenyl pyridine quaternary salt of bromomalonamide; the p-phenyl pyridine quaternary salt of bromomalonamide; the quinoline quaternary salt of 2-bromomalonamide and the polymeric quaternary salts prepared by quaternizing polyvinyl dimethyl amine with bromomalonamide.

The polymeric quaternary salt of this invention may be heated in solid form or in solution to provide cyanic acid and the polymeric carboxamide. If the reaction is run in solution the choice of solvent is limited by few parameters. In addition to being a solvent for the starting material, the solvent must not, of course, react with the starting material; nor should it react with the product. The boiling point of the solvent, at the pressure used, should be high enough so that the reaction can occur above about 100° C. and preferably at about 150°-170° C. without the solvent boiling. The reaction may, of course, be run in a closed system such as a steel bomb in a solvent with a lower boiling point. m-Cresol can be used as a solvent in this reaction.

A preferred embodiment of this invention involves the cracking of the pyridine quaternary salt of 2-methyl-2-bromomalonamide in m-cresol at 160°-170° C. which cracking yields only two isolatable products, cyanuric acid formed by the polymerization of cyanic acid and N-2 propionamido pyridinium bromide.

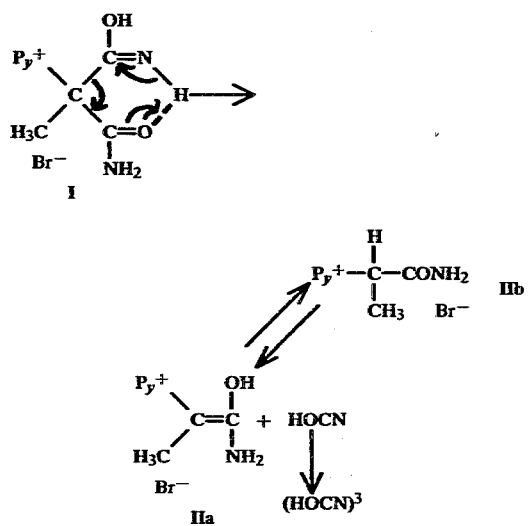

The above equation has been written with a cyclic hydrogen bonded structure for the quaternary salt (I) which uses the tautomeric form of one amide group. A mechanism similar to this equation can be written in which the cyclic hydrogen bonded structure involves the -OH of the tautomerized group rather than the imine residue, in which case tautomeric isocyanic acid (HNCO) would be split out. It is not known which mechanism prevails. Nor does this make a difference since cyanic and isocyanic acid normally are in tautomeric equilibrium with the iso-structure predominating. It is to be understood that neither the product nor the process of this invention is limited by this proposed mechanism.

There is reliable evidence that (I) does exist in some cyclic hydrogen bonded imino form, at least in the solid-state. The infrared spectra of primary amides normally contain two absorption bands in the 1600-1700 cm$^{-1}$ region which are assigned to carbonyl stretching and —NH$_2$ deformation. Spectra taken (KBr discs) of malonamide, 2-methyl-malonamide and 2-bromo-2-methyl malonamide, all contain these two absorptions. The infrared spectrum of (I) (KBr) disc) shows at least 7 bands in the 1600-1720 cm$^{-1}$ range. Comparison of this spectrum with that of deuterated I (dry KBr and Nujol mull;) shows that the band at 1627 cm$^{-1}$ has shifted slightly to 1630 cm$^{-1}$ and must be assigned to vibrations of the N-alkylated pyridinium ring which normally occur at this frequency. The 1600 cm$^{-1}$ band has been shifted to a much lower frequency and its origin is an N—H or NH$_2$ bending deformation. In the spectrum of deuterated I, at least five bands still remain between 1640 and 1700 cm$^{-1}$ and these undoubtedly arise from hydrogen bonded and nonhydrogen bonded carbonyl and imino forms of I. The infrared spectrum of (II) (KBr disc) is that of a normal primary amide since the possibility for cyclic hydrogen bonded structures is no longer present. Pyridinium ring absorption is again about 1630 cm$^{-1}$. The —C═O stretching vibration is at 1688 cm$^{-1}$ with the —NH$_2$ deformation appearing as a shoulder on the lower frequency side of the carbonyl absorption. If the infrared spectrum of (I) is taken in diimethylsulfoxide, an excellent solvating and hydrogen bond breaking solvent, the carbonyl and —NH$_2$ absorptions revert to those of a normal primary amide.

It has been shown that cyanic acid can be produced from solutions of these quaternary salts. For example, in our parent application Ser. No. 725,571, in a preferred embodiment there was provided a solution in m-cresol of an amine-substituted dye which dye must be stable at 150°-170° C. For example, a solution of 1-amino-4-hydroxy-anthraquinone may be provided and divided into two portions. To one portion is added the pyridine quaternary salt of 2-bromo-2-methylmalonamide. Each portion is then heated to approximately 160° for about an hour and then cooled. It is found that the portion containing the pyridine quaternary salt has changed color. It is more red in appearance than is the control portion. This change is consistent with the formation in the solution of the substituted urea

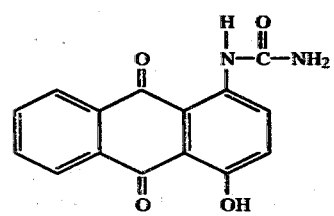

The decyanation reaction of this invention may be utilized to provide images by the imagewise thermal decyanation of a polymeric quaternary salt. In this embodiment, the polymer is intimately associated with a dye containing an amine group. This mixture of polymer and dye is provided in a layer which can be heated to approximately 150°-200° in an imagewise manner, for example, by contacting the layer with a metal form bearing a relief character, an image. Upon this thermal contact the polymer decyanates releasing cyanic acid which reacts with the amine group of the associated dye changing the color of the dye.

The present invention will be illustrated in greater detail in conjunction with the following specific examples which are intended to be illustrative only and should not be taken in a limiting sense.

EXAMPLE I

Diethyl methyl malonate was reacted with aqueous concentrated ammonia to yield 2-methyl-malonamide which, after recrystallization from methanol, had a melting point of 213°-14° (uncorr.). The infrared spectrum is the same as given by C. J. Pouchert, Spectrum 339F in the Aldrich Library of Infrared Spectra, Aldrich Chemical Co., 1970, and the nuclear magnetic resonance spectrum in dimethylsulfoxide integrated properly for the various protons. Bromination of 2-methyl malonamide was carried out with bromine in glacial acetic acid following Stevens and Ward as reported in *J. Chem. Soc.* vol. 125, page 1324 (1924). Two recrystallizations from methanol gave a melting point of 177° C. (uncorr.), reported 172° C.

The pyridine quaternary salt of 2-bromo-2-methyl-malonamide was readily prepared by dissolving the bromo compound in excess pyridine and heating the solution for several hours at 60° C.

The quaternary salt was filtered off and recrystallized twice from methanol, m.p.=227° C. (uncorr., with decomposition). The salt is water soluble and reacts instantly with silver nitrate solution. Analysis gave: C, 39.5; H, 4.59; N, 15.0; Br, 28.8. Theory: C, 39.4; H, 4.38; N, 15.3; Br, 29.2. $D_2O$ rapidly exchanges the amide protons, and NMR is in complete agreement with the assigned structure.

Decyanation was carried out as follows. The pyridine quaternary salt (0.5 g.) was dissolved in 5 ml. of warm m-cresol and the solution heated at 160°-70° C. for 50 min. in an oil bath. Evolved vapors are neutral to indicator paper. On cooling the solution in a refrigerator, a white solid separated from solution. This solid was filtered off, washed with a small amount of 1/1 methanol-ether and air dried. It did not melt up to 350° C. and was readily identified as pure cyanuric acid by comparison of its infrared spectrum (KBr disc) with that of an authentic sample. The m-cresol filtrate was poured with stirring into a large excess of diethyl ether. A tacky material separated, which was again reprecipitated from a very small amount of methanol into excess ether. The tacky precipitate was recrystallized from methanol/ether to yield a white crystalline solid having a m.p. of 189°-90° C. (uncorr.). It was readily water soluble and gave a strong test for soluble bromide. The NMR spectrum (in DMSO) is in complete agreement with the assigned structure for N-2-propionamideo pyridinium bromide. Analysis gave: C, 41.8; H, 4.89; N, 12.1; Br, 34.5. Theory: C, 41.6; H, 4.80; N, 12.1; Br, 34.6. In three repeats of this decyanation reaction, no other products were obtained. Depending on the exact conditions (relative concentrations of quaternary salt (1) and m-cresol, temperature and time), cyanuric acid may or may not be isolated. Therefore, cyanic acid may escape by volatization, or polymerize in situ; or it may react with added materials to give desired by-products. The yield of crude N-2-proionamido pyridinium bromide is almost quantitative.

EXAMPLE II

2-Bromomalonamide, m.p.=181° c., was prepared following Backes, West, and Whiteley, *J. Chem. Soc., Trans.* 1, volume 119, p. 359 (1921). The pyridine quaternary salt, m.p.=224°-5° C. (uncorr.) was prepared by heating bromomalonamide in methanol solution with excess pyridine. Analysis gave: C, 37.2; H, 3.92; N, 16.0; Br, 30.9. Theory: C, 36.9; H, 3.84; N, 16.1; Br. 30.8. Decyanation and isolation was carried out as described in Example I for the salt of 2-bromo-2-methyl-malonamide. The decyanation product, N-2-acetamido-pyridinium bromide, m.p.=200° C., (uncorr.), had the following analysis. Found: C, 39.3; H, 4.28; N, 13.1; Br, 37.0. Theory: C, 38.8; H, 4.15; N, 12.9; Br, 36.9.

EXAMPLE III

A polymeric quaternary salt, designated as Polyquat A, was prepared by quaternizing poly 4-vinylpyridine with bromomalonamide. Bromomalonamide (6 g, 0.033 m) dissolved in 100 ml. of hot methanol was added to a solution of poly 4-vinyl pyridine (10.5 g, 0.1 m) in 200 ml. of hot ethanol. The solution, heated on a steam cone, gelled afer ten minutes.

Heating was continued for an additional 30 minutes. The polymer was coagulated by adding excess acetone, washed successively with ethanol, acetone and ether and vacuum dried. The polymer is a yellow powder which dissolves in water to yield a yellow solution having a pH of about 7.5. The color suggests that the polymer exists partially as the polymeric ylid zwitterion.

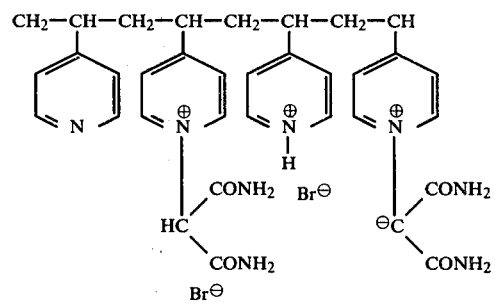

Addition of dilute acid to the aqueous solution bleaches the color whereas the addition of dilute alkali produces a deep yellow color. Polyquat A was 33% quaternized, based on elemental analysis for bromide.

A second polymeric quaternary salt, designated as Polyquat B was prepared similarly except that 100% quaternization was sought. Bromomalonamide (10 g., 0.055 m) in 150 ml. of hot methanol was added to a solution of poly 4-vinylpyridine (5 g., 0.047 m) dissolved in 150 ml. of ethanol. The solution was heated for 2 hours on a steam cone and the solvents allowed to almost completely distill off. Additional methanol was added and the swollen polymer filtered off, washed with hot methanol, ether and vacuum dried. The polymer is a very light yellow powder which dissolves in distilled water to give an almost colorless solution of about pH=5.6. The lighter color suggests that because of the higher degree of quaternization and lower free base content, less ylid structure is present. Elemental analysis of Polyquat B indicated 99.5% quaternization. Potentiometric analysis of bromine indicated a somewhat lower degree of quaternization.

Final purification of both Polyquats A and B was accomplished by dialysis of their stirred water solutions for several hours against distilled water using regenerated cellulose dialysis tubing. The polymers were isolated by freeze drying and final drying was accomplished at 45° C. under vacuum over phosphorus pentoxide.

Films of Polyquat B containing the disodium salt of 3,3'-[4,4' biphenylylene bis (azo)] bis[4-amino-1-naphthalenesulfonic acid] (known as Congo Red) were cast from water and air dried. These films were heated to about 170°–180° C. in film form on glass or pulverized in a capillary. In both cases there was an evident decrease in the color intensity and a hypsochromic shift in color. Congo Red heated in a capillary at the same time and rate did not show either change at this temperature.

EXAMPLE IV

One gram of 2-bromomalonamide (m.p. 181° C.) was heated with an excess of pure trimethylamine in a steel bomb at 100° C. for 18 hours. The solid in the bottom of the bomb after evaporation of the excess amine was recrystallized from ethanol containing a small amount of methanol; m.p=195°–6° C. with no foamsing. Above 200° C. the brom melt rises in the capillary. This product is water soluble and contains bromide ion. Analysis showed 33.1% Br (theoretical value 33.3% Br) for

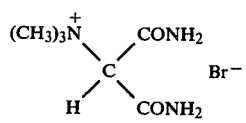

The infrared spectrum of the above compound shows a carbonyl stretch at 1720 cm$^{-1}$. Elemental analysis gave carbon 30.26%; hydrogen 5.99% and nitrogen 17.76%. Theoretical values are: carbon 30.0%, hydrogen 5.87% and nitrogen 17.5%. The NMR in deuterated dimethyl sulfoxide integrates properly.

One half gram of the quaternary salt of the above compound was dissolved in excess m-cresol (about 5 ml.), and heated for one hour at 160° C. in an oil bath. The product was precipitated into ether and recrystallized from alcohol/ether. The melting point was 181° C. but was not sharp. A mixed melting point with the above compound showed a large depression to about 160° C. showing that the product was not the above compound. The product is water soluble and contains bromide ions. Analysis for bromide gave 40.53% as opposed to a theoretical bromide value of 40.51% for the decyanated product

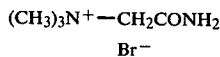

EXAMPLE V

Polyvinyl alcohol of a low degree of polymerization dissolved in m-cresol solution was treated with the pyridine quaternary salt of 2-methyl-2-bromomalonamide and the reaction mixture heated at 160°–170° C. for one hour. Polymer was recovered in a fibrous form by precipitation into methanol, was purified by two reprecipitations from water into a large excess of methanol and was dried under vacuum at 45° C. over phosphorous pentoxide. Analysis gave 1.15 percent nitrogen and the infrared spectrum indicates that the product is a copolymer of vinyl alcohol and vinyl carbamate. FIG. 1 is a graph of the infrared spectrum of (a) the starting material, polyvinyl alcohol (the dashed curve); and (b) the product formed after th decyanation and reaction of the liberated cyanic acid with the polyvinyl alcohol (the solid curve) showing it to be in the partial carbamate ester of polyvinyl alcohol.

EXAMPLE VI

One-half gram of the pyridine quaternary salt of 2-bromo-2-methylmalonamide as prepared in Example I was dissolved in 5 ml. of warm m-cresol and the solution heated at 112°–117° C. for 17 hours in an oil bath. After this heating the solution was poured with stirring into 100 ml. of ether. An almost white precipitate was filtered out and dissolved in a minimum amount of methanol. On a steam cone, ether was added to the methanol solution dropwise until a slight haze developed. The solution was allowed to cool, first to room temperature and then in a refrigerator. The crystals formed, representing about 20% of the starting material, were filtered off and dried. They melted in the temperature range 172°–185° C. Infrared analysis indicated that they were starting material contaminated with a little of the decyanation product. Washing these crystals with a small amount of methanol resulted in raising their m.p. range to 205°–215° C. The m.p. of pure starting material is 227° C.

The methanol filtrate was poured into an excess of ether. The precipitate formed, representing about 80% of the starting material, was collected and vacuum dried. It melted at 173°–182° C. The infrared spectrum was that of the decyanated product. Pure decyanated product melts at 180°–190° C.

It can be seen that by allowing longer reaction times the decyanation can be carried out at lower temperatures. This method of generating cyanic acid is thereby useful in situations wherein it is desired to react in situ generated cyanic acid with compounds which are not stable at much higher temperatures, or in situations wherein a slow release of in situ generated cyanic acid is desired.

EXAMPLE VII

The isoquinoline quaternary salt of 2-bromomalonamide was prepared by heating bromomalonamide in methanol solution with excess isoquinoline. A good yield of the quaternary salt was filtered off and recrystallized from methanol, m.p.=234° (uncorr.). It was water soluble and reacted instantly with silver nitrate solution. Carbonyl absorption was between 1700 and 1720$^{-1}$. Differential thermal analysis showed a transition at 130°–135° C., and a melting starting at 225° C. followed by the decyanation exotherm. Thermogravimetric analysis showed the start of a rapid gross decomposition at approximately 240° C.

EXAMPLE VIII

The isoquinoline quaternary salt of 2-bromo-2-methyl malonamide was prepared similiarly. It was water soluble, had a melting point of 186°–190° C., and reacted instantly with silver nitrate solution. The infrared spectrum showed a carbonyl absorption at 1700$^{-1}$. Differential thermal analysis showed melting beginning at 183° C. followed by the decyanation exotherm. Thermogravimetric analysis showed a rapid gross decomposition beginning at 198° C.

EXAMPLE IX

The quinoline quaternary salt of 2-bromomalonamide was prepared by heating a gram of 2-bromomalonamide with excess quinoline for 4 hours at 65° C., precipitating into ether, dissolving the precipitate in a minimum quantity of warm methanol, and adding ether to the point of haze formation. After decanting the solvent, methanol was added to the resulting oil to give crystals which melted at 210°–212° C. and showed a carbonyl absorption in their infrared spectrum at $1710^{-1}$. The product was water soluble and gave a good test for bromide ion, reacting instantly with silver nitrate solution. Differential thermal analysis showed a melting point at 207° C. followed by the decyanation exotherm. Thermogravimetric analysis showed rapid gross decomposition at approximately 225° C.

Since certain changes may be made in the above process without departing from the scope of the invention herein involved, it is intended that all matter contained in the above description or shown in the accompanying drawings shall be interpreted as illustrative and not in a limiting sense.

What is claimed is:

1. A polymeric compound of the structure

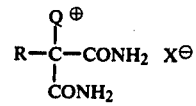

where Q is a polyvinyl pyridinium, R is hydrogen or a n-alkyl group containing from one to twenty carbon atoms inclusive and X is bromide, chloride or iodide.

2. A compound as defined in claim 1 wherein Q is poly-4-vinyl pyridinium.

3. A compound as defined in claim 2 wherein R is hydrogen and X is bromide.

* * * * *